United States Patent [19]
Solomon

[11] 3,948,994
[45] Apr. 6, 1976

[54] OXO- AND HYDROXY-SUBSTITUTED HYDRO STILBENES

[75] Inventor: Paul W. Solomon, Bartlesville, Okla.

[73] Assignee: Phillips Petroleum Company, Bartlesville, Okla.

[22] Filed: Apr. 21, 1975

[21] Appl. No.: 570,330

Related U.S. Application Data

[60] Division of Ser. No. 354,094, April 24, 1973, Pat. No. 3,897,501, which is a continuation-in-part of Ser. No. 714,070, March 18, 1968, Pat. No. 3,763,240, which is a continuation-in-part of Ser. No. 509,624, Nov. 24, 1965, abandoned.

[52] U.S. Cl. ............... 260/586 R; 71/123; 252/522; 260/33.4 R; 260/33.4 PQ; 260/89.5 R; 260/468 R; 260/586 P; 260/610 B; 260/617 R; 260/666 A; 260/666 PY

[51] Int. Cl.$^2$ ................. C07C 33/02; C07C 35/21; C07C 49/61

[58] Field of Search ............ 260/617 R, 586 R, 631

[56] References Cited
UNITED STATES PATENTS

| | | | |
|---|---|---|---|
| 2,392,864 | 1/1946 | Schoeller et al. ............... | 260/586 R |
| 3,527,815 | 9/1970 | Holtz ............................... | 260/617 R |
| 3,527,816 | 9/1970 | Morell ............................ | 260/617 R |

*Primary Examiner*—Norman P. Morgenstern

[57] ABSTRACT

Bicyclic triolefins are converted to peroxides, alchols and ketones.

3 Claims, No Drawings

OXO- AND HYDROXY-SUBSTITUTED HYDRO STILBENES

This application is a division of Ser. No. 354,094, filed Apr. 24, 1973, now U.S. Pat. No. 3,897,501 which was a continuation-in-part of application Ser. No. 714,070, filed Mar. 18, 1968, now U.S. Pat. No. 3,763,240, which in turn was a continuation-in-part application of application Ser. No. 509,624, filed Nov. 24, 1965, now abandoned.

This invention relates to a process for the production of novel triolefin hydroperoxides. In one aspect, it relates to the production of 1,2-bis(3-cyclohexen-1-yl)ethylene hydroperoxides. In another aspect, it relates to the production of alcohols through the reduction of said triolefin hydroperoxides. In another aspect, it relates to novel ketone derivatives of said triolefin hydroperoxides.

In a commonly assigned copending case (U.S. application Ser. No. 502,544, filed Oct. 22, 1965, now abandoned, and its continuation-in-part application Ser. No. 665,239, filed Sept. 5, 1967, now U.S. Pat. No. 3,463,828, issued Aug. 26, 1969), there is described a method for the preparation of novel triolefin compounds.

It is therefore an object of this invention to prepare novel triolefin hydroperoxide derivatives of said novel compounds produced in the above-identified application.

It is another object of this invention to provide a process for the production of novel alcohol derivatives of said triolefin compounds produced in the above-identified application.

It is another object of this invention to provide a process for the production of novel ketone derivatives of said triolefin compounds produced in the above-identified application.

It is yet another object of this invention to provide novel 1,2-bis-(3-cyclohexen-1-yl)ethylene hydroperoxides.

It is another object of this invention to provide novel alcohol derivatives of 1,2-bis(3-cyclohexen-1-yl)ethylene hydroperoxides.

It is still a further object of this invention to provide novel ketone derivatives of 1,2-bis(3-cyclohexen-1-yl)ethylene hydroperoxides.

Other objects and many of the attendant advantages of this invention will be readily appreciated as the same becomes better understood by reference to the following detailed description.

I have now discovered a process for the production of novel triolefin hydroperoxides, said process comprising the step of oxidizing a triolefin characterized by the following formula:

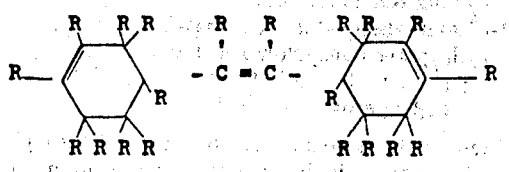

wherein R is selected from the group consisting of hydrogen, methyl and ethyl, wherein the total number of carbon atoms in all of said R groups does not exceed 8, and wherein at least one of said R groups which is in a position allylic to an olefinic double bond is hydrogen, with an oxygen-containing gas.

Specific examples of triolefins which are useful as the starting materials in the practice of this invention are as follows:

1,2-bis(3-cyclohexen-1-yl)ethylene
1,2-bis(1-methyl-3-cyclohexen-1-yl)ethylene
1,2-bis(2-methyl-3-cyclohexen-1-yl)ethylene
1,2-bis(3-ethyl-3-cyclohexen-1-yl)ethylene
1,2-bis(4-methyl-3-cyclohexene-1-yl)ethylene
1,2-bis(5-ethyl-3-cyclohexen-1-yl)ethylene
1,2-bis(6,6-dimethyl-3-cyclohexen-1-yl)ethylene
3,4-bis(3-cyclohexen-1-yl)-3-hexene
1,2-bis(2,6-dimethyl-3-cyclohexen-1-yl)ethylene
2,3-bis(3-methyl-3-cyclohexen-1-yl)-2-butene
1,2-bis(1,3-dimethyl-3-cyclohexen-1-yl)ethylene
2,3-bis(4-methyl-3-cyclohexen-1-yl)-2-butene
1,2-bis(1,4-dimethyl-3-cyclohexen-1-yl)ethylene
1,2-bis(5,6-dimethyl-3-cyclohexen-1-yl)ethylene
2,3-bis(1,3,4-trimethyl-3-cyclohexen-1-yl)-2-butene
1,2-bis(2,5,6-trimethyl-3-cyclohexen-1-yl)ethylene
1,2-bis(2,6-diethyl-3-cyclohexen-1-yl)ethylene
3,4-bis(4-ethyl-3-cyclohexen-1-yl)-3-hexene
1-(3-methyl-3-cyclohexen-1yl)-2-(2-methyl-6-ethyl-3-cyclohexen-1-yl)-ethylene
1-(3-cyclohexen-1-yl)-2-(2-methyl-3-cyclohexen-1-yl)ethylene.

The oxygen-containing gas can be selected from the group consisting of pure oxygen, a mixture of oxygen and an inert gaseous diluent such as nitrogen, air, and air enriched with oxygen. The gas is conveniently passed into the triolefin, preferably with good dispersion through stirring or other means of agitation, at a rate equal to or in excess of the rate at which the oxygen is consumed. It is generally desirable that the flow of oxygen-containing gas be discontinued, and the oxidation terminated, when not more than about 30 per cent of the triolefin has been oxidized in order to obtain maximum selectivity to monohydroperoxide products.

Although the temperature at which the oxidation is carried out can be varied over a wide range, the temperature will usually be within the range of about 20° to 200°C, generally being within the range of about 40° to 100°C. The higher temperatures provide a faster rate of reaction whereas the lower temperatures result in greater selectivity to mono-hydroperoxide product. The reaction time usually will be within the range of about 10 minutes to about 24 hours, generally being within the range of about 30 minutes to about 6 hours. If desired, a solvent, e.g. benzene, inert under the reaction conditions, can be used. The reaction pressure need be only sufficient to maintain the triolefin and/or solvent in substantially the liquid phase.

It is also within the scope of this invention that an initiator can be employed in the oxidation step in order to decrease the initial induction period during which hydroperoxide formation is relatively slow. Any of the initiators which are generally useful in the production of hydroperoxides can be employed. Examples of some suitable initiators are chemical initiators such as peroxides, hydroperoxides, and azobisisobutyronitrile; ultraviolet light; and metal-containing compounds such as cobalt naphthenate, cupric oxide, and the like.

The hydroperoxides produced in accordance with the above-identified process have the following generic formulas:

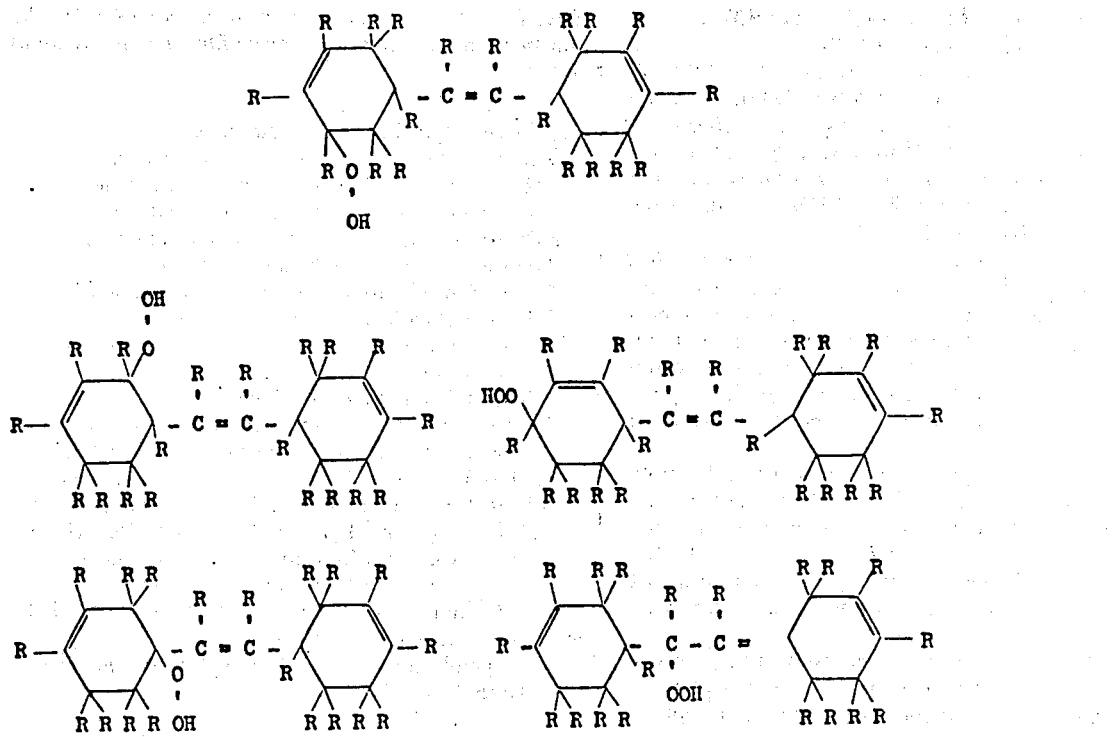

wherein R is selected from the group consisting of hydrogen, methyl and ethyl and wherein the total number of carbon atoms in all of said R groups does not exceed eight. Specific examples of novel hydroperoxides produced as described hereinabove are as follows:

1(3-cyclohexen-1-yl)2-(1hydroperoxy-3-cyclohexen-1-yl)ethylene
1-(3-cyclohexen-1-yl)-2-(2-hydroperoxy-3-cyclohexen-1-yl)ethylene
1-(3-cyclohexen-1-yl)2-(5-hydroperoxy-3-cyclohexen-1-yl)ethylene
1-(1-methyl-3-cyclohexen-1-yl)-2-(1-methyl-5-hydroperoxy-3-cyclohexen-1-yl)ethylene
1-(2-methyl-3-cyclohexen-1-yl)-2-(2-methyl-2hydroperoxy-3-cyclohexen-3-yl)ethylene
1-(3-ethyl-3-cyclohexen-1-yl)-2-(3-ethyl-1hydroperoxy-3-cyclohexen-1-yl)ethylene
1-(4-methyl-3-cyclohexen-1-yl)-2-(4-methyl-2-hydroperoxy-3-cyclohexen-1-yl)ethylene
1-(5-ethyl-3-cyclohexen-1-yl)-2-(5-ethyl-5-hydroperoxy-3-cyclohexen-1-yl)ethylene
1-(6,6-dimethyl-3-cyclohexen-1-yl)-2-(6,6-dimethyl-2-hydroperoxy-3-cyclohexen-1-yl)ethylene
3-(3-cyclohexen-1-yl)4-(5-hydroperoxy-3-cyclohexen-1-yl)-3-hexene
1-(2,6-dimethyl-3-cyclohexen-1-yl)-2-(2,6-dimethyl-2-hydroperoxy-3-cyclohexen-1-yl)ethylene
2-(3-methyl-3-cyclohexen-1-yl)-3-(3-methyl-1-hydroperoxy-3-cyclohexen-1-yl)-2-butene
1-(1,3-dimethyl-3-cyclohexen-1-yl)-2-(1,3-dimethyl-5-hydroperoxy-3-cyclohexen-1-yl)ethylene
2-(4-methyl-3-cyclohexen-1-yl)3-(4-methyl-1-hydroperoxy-3-cyclohexen-1-yl)-2-butene
1-(1,4-dimethyl-3-cyclohexen-1-yl)-2-(1,4-dimethyl-2-hydroperoxy-3-cyclohexen-1-yl)ethylene
1-(5,6-dimethyl-3-cyclohexen-1-yl)-2-(5,6-dimethyl-1-hydroperoxy-3-cyclohexen-1-yl)ethylene
2-(1,3,4-trimethyl-3-cyclohexen-1-yl)-3-(1,3,4-trimethyl-5-hydroperoxy-3-cyclohexen-1-yl)-2-butene
1-(2,5,6-trimethyl-3-cyclohexen-1-yl)-2-(2,5,6-trimethyl-1-hydroperoxy-3-cyclohexen-1-yl)ethylene
1-(2,6-diethyl-3-cyclohexen-1-yl)-2-(2,6-diethyl-2-hydroperoxy-3-cyclohexen-1-yl)ethylene
1-hydroperoxy-1-(2,6-diethyl-3-cyclohexen-1-yl)-2-(2,6-diethyl-3-cyclohexenylidene)ethane
3-(4-ethyl-3-cyclohexen-1-yl)-4-(4-ethyl-5-hydroperoxy-3-cyclohexen-1-yl)-3-hexene
1-(2-methyl-6-ethyl-3-cyclohexen-1-yl)-2-(3-methyl-1-hydroperoxy-3-cyclohexen-1-yl)ethylene
1-(3-cyclohexen-1-yl)2-(2-methyl-2-hydroperoxy-3-cyclohexen-1-yl)-ethylene
1-(3-cyclohexen-1-yl)-2-(4-hydroperoxy-2-cyclohexen-1-yl)ethylene
1-hydroperoxy-1-(3-cyclohexen-1-yl)-2-(3-cyclohexenylidene)ethane
1-(3-methyl-3-cyclohexen-1-yl)-2-(3-methyl-4-hydroperoxy-2-cyclohexen-1-yl)ethylene These hydroperoxides can be reduced through the use of suitable reducing agents such as sodium sulfite, hydrazine, tertiary amines, triphenyl phosphine, hydrogen (with a suitably supported catalyst), lithium aluminum hydride, sodium borohydride, and the like in order to produce the corresponding unsaturated alcohols.

Alcohols produced by the process of this invention are represented by the following formulas:

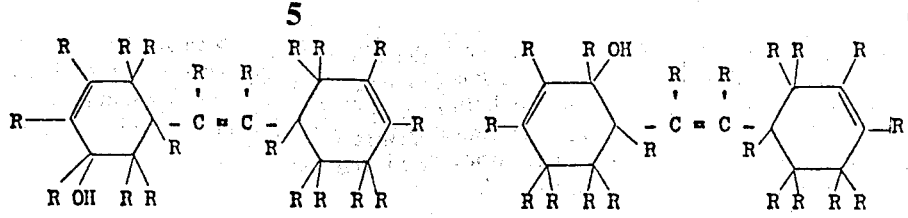

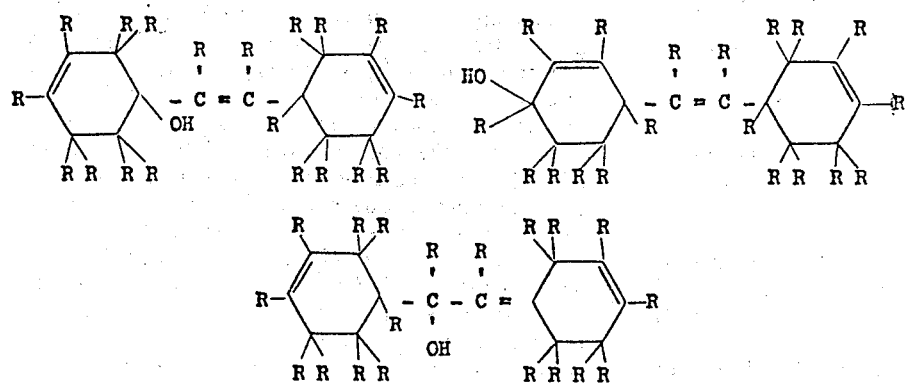

wherein R is selected from the group consisting of hydrogen, methyl and ethyl and wherein the total number of carbon atoms in all of said R groups does not exceed eight.

Specific examples of mono-ols produced in the practice of this invention are as follows:

1-(3-cyclohexen-1-yl)-2-(1-hydroxy-3cyclohexen-1-yl)ethylene
1-(3-cyclohexen-1-yl)-2-(2-hydroxy-3-cyclohexen-1-yl)ethylene
1-(3-cyclohexen-1-yl)-2-(5-hydroxy-3-cyclohexen-1-yl)ethylene
1-(1-methyl-3-cyclohexen-1-yl)-2-(1-methyl-5-hydroxy-3-cyclohexen-1-yl)ethylene
1-(2-methyl-3-cyclohexen-1-yl)-2-(2-methyl-2-hydroxy-3-cyclohexen-1-yl)ethylene
1-(3-ethyl-3-cyclohexen-1-yl)-2-(3-ethyl-1-hydroxy-3-cyclohexen-1-yl)ethylene
1-(4-methyl-3-cyclohexen-1-yl)-2-(4-methyl-2-hydroxy-3-cyclohexen-1-yl)ethylene
1-(5-ethyl-3-cyclohexen-1-yl)-2-(5-ethyl-5-hydroxy-3-cyclohexen-1-yl)ethylene
1-(6,6-dimethyl-3-cyclohexen-1-yl)-2-(6,6-dimethyl-2-hydroxy-3-cyclohexen-1-yl)ethylene
3-(3-cyclohexen-1-yl)-4-(5-hydroxy-3-cyclohexen-1-yl)-3-hexene
1-(2,6-dimethyl-3-cyclohexen-1-yl)-2-(2,6-dimethyl-2-hydroxy-3-cyclohexen-1-yl)ethylene
2-(3-methyl-3-cyclohexen-1-yl)-3-(3-methyl-1-hydroxy-3-cyclohexen-1-yl)-2-butene
1-(1,3-dimethyl-3-cyclohexen-1-yl)-2-(1,3-dimethyl-5-hydroxy-3-cyclohexen-1-yl)ethylene
2-(4-methyl-3-cyclohexen-1-yl)-3-(4-methyl-1-hydroxy-3-cyclohexen-1-yl)-2-butene
1-(1,4-dimethyl-3-cyclohexen-1-yl)-2-(1,4-dimethyl-2-hydroxy-3-cyclohexen-1-yl)ethylene
1-(5,6-dimethyl-3-cyclohexen-1-yl)-2-(5,6-dimethyl-1-hydroxy-3-cyclohexen-1-yl)ethylene
2-(1,3,4-trimethyl-3-cyclohexen-1-yl)-3-(1,3,4-trimethyl-5-hydroxy-3-cyclohexen-1-yl)-2-butene
1-(2,5,6-trimethyl-3-cyclohexen-1-yl)-2-(2,5,6-trimethyl-1-hydroxy-3-cyclohexen-1-yl)ethylene
1-(2,6-diethyl-3-cyclohexen-1-yl)-2-(2,6-diethyl-2-hydroxy-3-cyclohexen-1-yl)ethylene
1-hydroxy-1-(2,6-diethyl-3-cyclohexen-1-yl)-2-(2,6-diethyl-3-cyclohexenylidene)ethane
3-(4-ethyl-3-cyclohexen-1-yl)-4-(4-ethyl-5-hydroxy-3-cyclohexen-1-yl)-3-hexene
1-(2-methyl-6-ethyl-3-cyclohexen-1-yl)-2-(3-methyl-1-hydroxy-3-cyclohexen-1-yl)ethylene
1-(3-cyclohexen-1-yl)-2-(2-methyl-2-hydroxy-3-cyclohexen-1-yl)-ethylene
1-(3-cyclohexen-1-yl)-2-(4-hydroxy-2-cyclohexen-1-yl)ethylene
1-hydroxy-1-(3-cyclohexen-1-yl)-2-(3-cyclohexenylidene)ethane
1-(3-methyl-3-cyclohexen-1-yl)-2-(3-methyl-4-hydroxy-2-cyclohexen-1-yl)ethylene Those unsaturated alcohols having a hydrogen atom on the carbon atom to which the hydroxy group is attached can then be oxidized in a suitable oxidation system such as chromic oxide in acetone to provide novel unsaturated ketone derivatives of the starting triolefin material. These ketone compounds are represented by the following generic formulas:

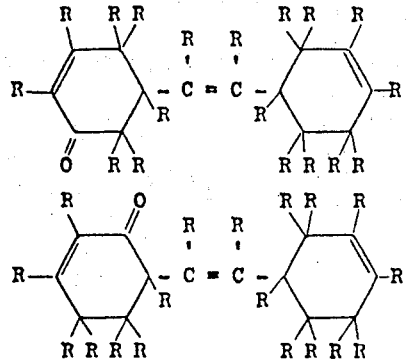

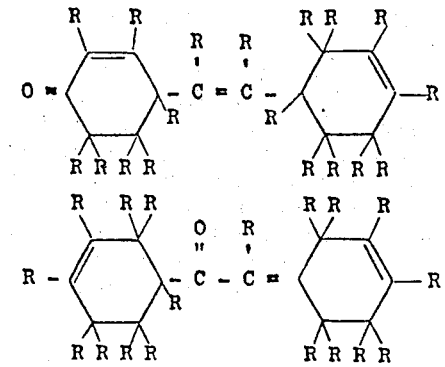

wherein R is selected from the group consisting of hydrogen, methyl and ethyl and wherein the total number of carbon atoms in all of said R groups does not exceed 8.

Specific examples of unsaturated ketones are:
1-(3-cyclohexen-1-yl)-2-(2-oxo-3-cyclohexen-1-yl)ethylene
1-(3-cyclohexen-1-yl)-2-(5-oxo-3-cyclohexen-1-yl)ethylene
1-(3-cyclohexen-1-yl)-2-(4-oxo-2-cyclohexen-1-yl)ethylene
1-oxo-1-(3-cyclohexen-1-yl)-2-(3-cyclohexenylidene)ethane
1-(1-methyl-3-cyclohexen-1-yl)-2-(1-methyl-5-oxo-3-cyclohexen-1-yl)ethylene
1-(4-methyl-3-cyclohexen-1-yl)-2-(4-methyl-2-oxo-3-cyclohexen-1-yl)ethylene
1-(6,6-dimethyl-3-cyclohexen-1-yl)-2-(6,6-dimethyl-2-oxo-3-cyclohexen-1-yl)ethylene
3-(3-cyclohexen-1-yl)-4-(5-oxo-3-cyclohexen-1-yl)-3-hexene
1-(1,3-dimethyl-3-cyclohexen-1-yl)-2-(1,3-dimethyl-5-oxo-3-cyclohexen-1-yl)ethylene
1-(1,4-dimethyl-3-cyclohexen-1-yl)-2-(1,4-dimethyl-2-oxo-3-cyclohexen-1-yl)ethylene
1-(1,3,4-trimethyl-3-cyclohexen-1-yl)-3-(1,3,4-trimethyl-5-oxo-3-cyclohexen-1-yl)-2-butene
3-(4-ethyl-3-cyclohexen-1-yl)-4-(4-ethyl-5-oxo-3-cyclohexen-1-yl)-3-hexene
1-(2-methyl-5-ethyl-3-cyclohexen-1-yl)-2-(6-methyl-4-oxo-2-cyclohexen-1-yl)ethylene
1-(3-cyclohexen-1-yl)-2-(4-methyl-2-oxo-3-cyclohexen-1-yl)ethylene
1-(3-methyl-3-cyclohexen-1-yl)-2(3-methyl-4-oxo-2-cyclohexen-1-yl)ethylene
1-oxo-1-(2,6-diethyl-3-cyclohexen-1-yl)-2-(2,6-diethyl-3-cyclohexenylidene)ethane.

The ketones produced according to the process as described hereinabove have a pleasant rose-like odor and can be utilized as rose-odor additives. These ketones can also be used in the preparation of compounds for agricultural use. The unsaturated ketones of this invention can be hydrogenated in a known manner (Chemical Abstracts, Vol. 51, column 244d, 1957) to yield the saturated ketone and the saturated ketone can be sprayed onto soil as an effective soil fungicide. For example, the 1-(3-cyclohexen-1-yl)2-(5-oxo-3-cyclohexen-1-yl)ethylene of Example V hereinafter can be formed into the corresponding saturated ketone, i.e., 3-(2-cyclohexylethyl)cyclohexanone, and when this saturated ketone was sprayed in the amount of 48 pounds of ketone per acre onto soil infested with *Rhizoctonia solani* fungus, the fungus was sufficiently killed to allow a major amount of seeds in the soil, e.g., pea seeds (*Pisum sativum* L. var. Perfection), to germinate and grow into healthy plants, see Example VI hereinafter.

The unsaturated alcohols of this invention can be used in a number of applications which involve one or more of the olefinic double bonds and/or hydroxyl groups. For example, acrylic acid or methacrylic acid can be esterified with the unsaturated alcohols and the esters thus produced can be polymerized to yield polymers having a greater number of cross linkages than occur in the usual polyacrylate or polymethacrylate resins. Additionally, the esterified unsaturated alcohols can be used as plasticizers for synthetic resins such as polyethylene or polyvinyl chloride.

The following examples describing specific embodiments of this invention are given by way of illustration only, and obviously may be modified considerably as to catalyst employed, operating conditions, and quantitative relationships, without departing from the spirit and scope of the invention.

EXAMPLE I

A stream of oxygen was passed for 2 hours into 230 g. of trans-1,2-bis(3-cyclohexen-1-yl)ethylene (88 weight percent purity) containing 20 g. of cupric oxide (freshly ground in vacuo in a ball mill) at 65°–67°C with vigorous stirring. The rate of oxygen consumption increased as the reaction progressed, being practically nil initially and increasing to 20 ml/min. at the end of 1 hour, 43 ml/min. at the end of 1½ hours, 51 ml/min. at the end of 1¾ hours, and 57 ml/min. at the end of 2 hours. At the end of the 2-hour reaction period, during which the 0.12 mol of oxygen was consumed, the mixture was filtered hot through an 0.8 micron millipore filter to remove the cupric oxide from the light yellow solution. Analysis of the filtrate by the method of Siggia, "Quantitative Organic Analysis via Functional Groups", 2nd Edition, John Wiley and Sons, Inc., New York (1954), p. 150, showed the presence of 0.077 mol of hydroperoxides, representing a 64 mol per cent yield based on the oxygen consumed. The solution of hydroperoxides was refluxed for 30 minutes with a solution of 25 g. (0.2 mol) of sodium sulfite in 200 ml of water to reduce the hydroperoxides to the corresponding alcohols. Approximately two-thirds of the hydrocarbon layer was separated from the aqueous layer, washed three times with water, and dried over magnesium sulfate. After removal of unreacted triolefin from the dried solution, the product was distilled to give 4.1 g. of a fraction boiling at 105°–108°C/0.13 mm and 1.1 g. of a second fraction boiling at 108°–120°C/0.13 mm; 2.3 g. of resinous material remained as a residue.

The following analysis of the fraction boiling at 105°–108°C/0.13 mm Hg was carried out to establish the identity of the product. Nuclear magnetic resonance analysis of the fraction gave results consistent with those to be expected for a mixture of 1,2-bis(3-cyclohexen-1-yl)ethylene having a single hydroxyl group in a position allylic to an olefinic double bond. The results are summarized in Table I.

TABLE I

| | Proton Distribution* | | | |
|---|---|---|---|---|
| | $H^a$ and $H^b$ | $H^c$ | $H^d$ | $H^e$ |
| Found | 5.6 | 1.0 | 0.9 | 12.5 |
| Theory | 6 | 1 | 1 | 12 |

*Designations for proton type are as follows:
$H^a$ = cyclic non-terminal olefinic protons
$H^b$ = non-cyclic non-terminal olefinic protons
$H^c$ = hydroxyl protons
$H^d$ = protons on carbons attached to hydroxyl groups
$H^e$ = all other protons These types are illustrated in the following example:

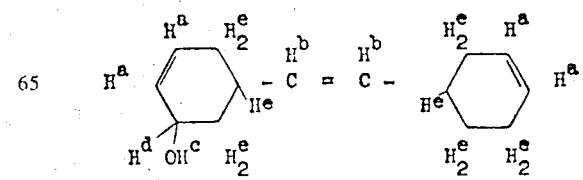

Elemental analysis of the fraction showed the weight percent of carbon and hydrogen to be 82.2 and 9.8, respectively, compared with calculated values of 82.3 and 9.8, respectively, for a mixture of 1,2-bis(3-cyclohexen-1-yl)-ethylenes having a single hydroxyl group in a position allylic to an olefinic double bond. The molecular weight, by osmometry, of this fraction was 203, compared with a calculated value of 204 for the above mixture of hydroxy compounds. The molecular weight by mass spectrometer analysis was 204. Infrared analysis of the fraction indicated the degree of olefinic unsaturation to be approximately the same as that of the triolefin reactant. Strong absorption at 2.9 and 9.5 microns indicated the presence of secondary hydroxyl groups. A small amount of substance containing a carbonyl group conjugated with an olefinic double bond was indicated by weak absorption at 5.95 microns.

EXAMPLE II

Five hundred grams (2.66 mols) of 1,2-bis(3-cyclohexen-1-yl)ethylene (BCE) was placed in a three-necked, 1-liter Morton flask equipped with condenser, thermometer and hollow Truebore stirrer and heated to about 65°C. With vigorous stirring a metered stream of oxygen was passed into the triolefin, and the off gases from the condenser were passed through a dry ice trap and a wet-test meter. Oxygen flow was regulated such that a positive pressure was maintained in the system. After approximately 4 hours, a granular, sticky solid began precipitating on the flask walls. The reaction was terminated after 6½ hours. At this time 15140 ml (0.62 mol) of oxygen had been consumed. The product, a light yellow liquid, was filtered to remove the suspended granular material. The granular material adhering to the flask walls was washed with n-pentane as was that on the filter paper. The solvent was evaporated and the recovered additional liquid added to the main filtrate. The precipitate weighed 2.0 grams and the filtrate weighed 515 grams.

Titration of the liquid product with $As_2O_3$ gave a hydroperoxide content of 20.4 ± 0.3 weight percent calculated as monohydroperoxy-substituted 1,2-bis(3-cyclohexen-1-yl)ethylene, or 0.48 mol. Only a trace of liquid product was recovered from the dry ice trap in the exit gas line. The hydroperoxide product comprised a mixture of 1-(3-cyclohexen-1-yl)-2-(1-hydroperoxy-3-cyclohexen-1-yl)ethylene, 1-(3-cyclohexen-1-yl)-2-(2-hydroperoxy-3-cyclohexen-1-yl)ethylene, 1-(3-cyclohexen-1-yl)-2-(5-hydroperoxy-3-cyclohexen-1-yl)ethylene, 1-(3-cyclohexen-1-yl)-2-(4-hydroxy-2-cyclohexen-1-yl)ethylene, and 1-hydroperoxy-1-(3-cyclohexen-1-yl)-2-(3-cyclohexenylidene)ethane.

EXAMPLE III

The product obtained in Example II, product A, was divided into five equal parts and each part selectively hydrogenated according to the following procedure. One hundred and three grams was dissolved in 100 ml of ethanol and placed in a Brown hydrogenator with 0.4 gram of palladium catalyst poisoned with lead. In three of the five runs 0.05–0.4 gram of quinoline was added in order to make the hydrogenation more selective for hydroperoxide over olefinic unsaturation. However, the hydrogenation rate was poor when quinoline was present. Therefore, no quinoline was used in the final two runs and the hydrogenation was stopped slightly past the hydrogen uptake value for total —OOH reduction. The five products from these hydrogenations contained only 3 to 5 weight percent 1,2-bis(3-cyclohexen-1-yl)ethylene hydroperoxides by $As_2O_3$ titration.

The five products were combined, filtered to remove catalyst, and solvents were evaporated in vacuum on a rotating evaporator. The combined products weighed 492 grams. Adding in the 13 grams which was used for analytical purposes indicated that a total of 505 grams of product was produced. Approximately 8 grams (0.24 mol) of $O_2$ was lost by reduction so that the actual amount of product expected would have been 507 grams. Two grams of suspended solid was removed from the product by filtration and the resulting material (490 grams) fractionated on an 18-inch glass helices packed column at 0.2–0.6 mm pressure and a 5:1 reflux ratio. Cuts were analyzed by boiling point, refractive index, GLC and GLC/mass combination to give the following approximate analysis:

| Fraction | Boiling Point, °C | $n_D^{20}$ | Grams | Grams BCE | Grams Dihydro BCE* | Grams Mono-oxy Products | Grams "High Boiler" |
|---|---|---|---|---|---|---|---|
|   | 78–83 | 1.5096–1.5099 | 331 | 314 | 17 | — | — |
| B | 83–165 | 1.5100–1.5328 | 130 | 53 | 1 | 71 | 5 |
|   | 165–200 | — | 9 | — | — | — | 9 |
|   | Residue | — | 15 | — | — | — | 15 |
|   | Total |   | 485 | 367 | 18 | 71 | 29 |
|   | Fractionation Loss |   | 5 |   |   |   |   |

*Mass/GLC combination characterized this material which occurs as a single peak eluting before 1,2-bis(3-cyclohexen-1-yl)-ethylene by GLC as 1-cyclohexyl-2-(3-cyclohexen-1-yl)ethylene.

Selectivity of the hydrogenation for hydroperoxide over olefinic double bonds was fair even though quinoline was not used.

If the 13 grams of material used for analytical determinations for hydroperoxide is distributed as above and the 2 portions of precipitated material (4 grams) removed by filtration are considered as "High Boiler" and the loss due to fractionation is added back proportionately, the following distribution is obtained:

|   | Grams |
|---|---|
| BCE + Dihydro-BCE | 400 |
| Mono-oxy Products | 74 |
| High Boiler | 33 |
| Total | 507 |

Therefore, olefin conversion was 20 percent and of the oxygenated products obtained, 67 percent were mono-oxy products comprising alcohols and ketones.

Specifically, Fraction B comprised a mixture of a major amounts of olefinically unsaturated alcohols, 1-(3-cyclohexen-1-yl)-2-(1-hydroxy-3-cyclohexen-1-yl)ethylene, 1-(3-cyclohexen-1-yl)-2-(2-hydroxy-3-cyclohexen-1-yl)ethylene, 1-(3-cyclohexen-1-yl)-2-(5-hydroxy-3-cyclohexen-1-yl)ethylene, 1-(3-cyclohexen-1-yl)-2-(4-hydroxy-2-cyclohexen-1-yl)ethylene, and 1-hydroxy-1-(3-cyclohexen-1-yl)-2-(3-cyclohexenylidene)ethane, and minor amounts of olefinically unsaturated ketones, 1-(3-cyclohexen-1-yl)-2-(2-oxo-3-cyclohexen-1-yl)ethylene, 1-(3-cyclohexen-1-yl)-2-(5-oxo-3-cyclohexen-1-yl)ethylene, 1-(3-cyclohexen-1-yl)-2-(4-oxo-2-cyclohexen-1-yl)ethylene, and 1-oxo-1-(3-cyclohexen-1-yl)-2-(3-cyclohexenylidene)ethane.

The mixture comprising Fraction B was converted entirely to the saturated ketones and compared with a mixture of the same saturated ketones which had been individually prepared by another method and authenticated by various types of analysis. Comparisons of the two mixtures by Thin Layer Chromatography and Gas Liquid Chromatography established that the mixtures contained the same compounds.

EXAMPLE IV

Thirty-nine grams of the mono-oxy product of Example III (approximately 0.1 mol of oxygenated product) was dissolved in 100 ml of commercial dry ether and dropped into a stirred solution of 5.7 grams (0.15 mole) of lithium aluminum hydride dissolved in 150 ml of ether held at 25°C in a 3-neck flask equipped with condenser, dropping funnel and Truebore stirrer. Reaction was mild indicating very little carbonyl compound was present. After the addition of the product from Example III, stirring was continued for 30 minutes. The mixture was poured into 1 liter of ice-water containing 100 ml of $H_2SO_4$. After decomposition of the complex, the aqueous phase was extracted 3 times with ether, the ether phases combined and washed with $H_2O$ and saturated $NaHCO_3$ solution, and the ether evaporated to yield 39.2 grams of yellow oil. This oil was dissolved in a small amount of cyclohexane and chromatographed on 800 grams of alumina with cyclohexane, then methanol as eluants. After removal of the solvents in vacuo on a rotating evaporator, 17.2 grams of material was recovered from the cyclohexane solution which analyzed as slightly hydrogenated 1,2-bis(3-cyclohexen-1-yl)ethylene by infrared. Twenty-one grams of material was recovered from the methanol solution which was distilled to give two fractions —C— b.p. — 122°–136°C/1 mm weighing 18.7 g., $n_D^{20}$ — 1.5242, water white, and D — b.p. — 127°–140°C/0.1 mm weighing 1.4 g., yellow, very viscous, — and 0.5 g. of residue.

The following analytical data were obtained for C, which comprised a mixture of the isomeric alcohols 1-(3-cyclohexen-1-yl)-2-(2-hydroxy-3-cyclohexen-1-yl)ethylene, 1-(3-cyclohexen-1-yl)-2-(2-hydroxy-3-cyclohexen-1-yl)ethylene, 1-(3-cyclohexen-1-yl)-2-(5-hydroxy-3-cyclohexen-1-yl)ethylene, 1-(3-cyclohexen-1-yl)-2-(4-hydroxy-2-cyclohexen-1-yl)ethylene, and 1-hydroxy-1-(3-cyclohexen-1-yl)-2-(3-cyclohexenylidene)ethane.

|  | Theory | Found |
|---|---|---|
| %C | 82.3 | 81.9 |
| %H | 9.8 | 9.8 |
| Osmometric Molecular Weight | 204 | 203 |

The infrared spectrum of C was consistent with that to be expected for unsaturated alcohols. No carbonyl absorbance was noted. Mass spectrographic analysis showed only a small 204 parent peak with a large 186 peak, characteristic of alcohols which lose a molecular of $H_2O$ readily. Nuclear magnetic resonance analysis gave the following proton distribution:

| Type of Protons | Number of Protons | |
|---|---|---|
|  | Theory | Found |
| Cyclic Olefinic | 4.0 | 3.7 |
| Ethylenic | 2.0 | 1.6 |
| —OH Protons | 1.0 | 1.1 |
| Protons alpha to —OH |  | 0.7 |
| Other Protons | 13.0 | 12.9 |

The slightly low olefinic proton values are indicative of the partial non-selectivity of the hydroperoxide hydrogenation. The ratio "Protons alpha to —OH"/"—OH Protons" indicates a ratio of 7/4 for secondary/tertiary alcohols.

EXAMPLE V

The product of Example IV was oxidized according to the following procedure. Ten and two-tenths grams (0.05 mol) of the product was dissolved in 10 ml of acetone and a solution of 3.0 grams (0.03 mol) of $CrO_3$ and 2.5 ml of $H_2SO_4$ in 9 ml of water was slowly added with stirring, keeping the temperature at 5°–10°C by means of an ice bath. The solution was dark blue-green after all of the $CrO_3$ solution was added. It was immediately diluted with an equal volume of $H_2O$, ether extracted three times, the combined ether phases washed with water and saturated $NaHCO_3$ solution, and the ether evaporated to give 10.1 grams of oil. Distillation of the oil gave two fractions — E— b.p. — 119°–132°C/1.0 mm weighing 8.1 g., $n_D^{20}$ — 1.5246, fruity-odored, pale yellow, and F— b.p., >132°C/1.0 mm weighing 0.4 g. The pot residue weighed 0.5 g.

Analytical data were obtained on E, which comprised a mixture of the tertiary alcohol 1-(3-cyclohexen-1-yl)-2-(1-hydroxy-3-cyclohexen-1-yl)ethylene and the ketones 1-(3-cyclohexen-1-yl)-2-(2-oxo-3-cyclohexen-1-yl)ethylene, 1-(3-cyclohexen-1-yl)-2-(5-oxo-3-cyclohexen-1-yl)ethylene, 1-(3-cyclohexen-1-yl)-2-(4-oxo-2-cyclohexen-1-yl)ethylene, and 1-oxo-1-(3-cyclohexen-1-yl)-2-(3-cyclohexenylidene)ethane.

|  | Theory* | Found |
|---|---|---|
| %C | 82.9 | 82.0 |
| %H | 9.2 | 9.4 |
| Osmometric Molecular Weight | 203 | 204 |

*Calculated as containing 36 per cent tert-alcohol and 64 per cent mixed ketones, as would be expected from the 7/4 secondary/tertiary alcohol ratio in C.

The infrared spectrum was consistent with the presence of olefinic unsaturation allylic to carbonyl and of hydroxyl groups. Mass spectrographic analysis indicated a large amount of the four expected oxo-substituted derivatives of 1,2-bis(3-cyclohexen-1-yl)ethylene, evidenced by a large 202 parent peak. A smaller amount of a hydroxy-substituted derivative of 1,2-bis(3-cyclohexen-1-yl)ethylene was indicated by the presence of a 186 peak which would not be expected from the ketones. Nuclear magnetic resonance analysis gave the following proton distribution:

| Proton Type | % Protons Theory[b] | Found |
|---|---|---|
| Aromatic | 2.7 | 2.9 |
| Olefinic[a] | 28.7 | 24.7 |
| Protons from —OH | 2.1 | 2.1 |
| Other protons | 66.5 | 70.3 |

[a]Both cyclic olefinic and ethylenic protons present; peaks overlap.
[b]Figured on the basis of 10 per cent 3-(2-phenylethyl)-cyclohexanone, 40 per cent

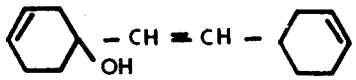

and 50 per cent mixed oxo-substituted derivatives of 1,2-bis(3-cyclohexen-1-yl)ethylene.

EXAMPLE VI

The ketone 3-(2-cyclohexylethyl)cyclohexanone, which is the saturated ketone that corresponds to 1-(3-cyclohexen-1-yl)-2-(5-oxo-3-cyclohexen-1-yl)ethylene of Example V hereinabove, was used in a soil fungicide test.

In the test, 1000 grams of autoclaved soil was mixed with 50 grams of a cornmeal-sand-water (weight ratios of 7/6/5, respectively) mixture which was infested with *Rhizoctonia solani* in a plastic bag.

The infested soil was then transferred to 4-inch vacuum-formed plastic pots, and 25 pea seeds (*Pisum sativum* L. var. Perfection) were placed in a ½-inch depth, one pea seed in each pot.

The soil in each pot was then drenched with 25 milliliters of a liquid which contained 0.15 milliliter of the ketone, 4 milliliters of acetone, 2 milliliters of "TRITON" X-155 (0.5 weight percent "TRITON" X-155 in water by volume) and 94 milliliters of distilled water. This amount of the ketone-containing liquid was equivalent to a concentration of active ketone of 48 pounds per acre.

After a period of 14 to 18 days, the 25 pots were observed and 80 percent contained viable plants thereby indicating that in 80 percent of the cases where the solution of the ketone was used, the fungus was sufficiently killed to allow the pea seed to germinate and a healthy plant grow therefrom. The concentration of fungus in the soil of each pot was sufficient, absent the application of the ketone solution, to prevent the growth of a plant from any of the 25 test seeds.

Obviously, many modifications and variations of the present invention are possible in the light of the above teachings. It is therefore to be understood that within the scope of the appended claims the invention may be practiced otherwise than as specifically described herein.

I claim:
1. 1-oxo-1-(3-cyclohexen-1-yl)-2-(3-cyclohexenylidene)ethane.
2. Unsaturated mono-ols characterized by the following formula:

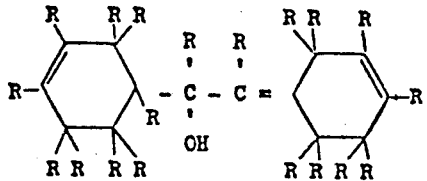

wherein R is independently selected from the group consisting of hydrogen, methyl and ethyl and wherein the total number of carbon atoms in all of said R groups does not exceed 8.
3. A mono-ol as defined in claim 2 which is 1-hydroxy-1-(3-cyclohexen-1-yl)-2-(3-cyclohexenylidene)ethane.

* * * * *